US011291624B2

(12) United States Patent
Gu et al.

(10) Patent No.: US 11,291,624 B2
(45) Date of Patent: Apr. 5, 2022

(54) COMPOSITIONS COMPRISING ACTIVE BOTANICAL INGREDIENTS

(71) Applicant: CONOPCO, INC., Trumbull, CT (US)

(72) Inventors: Xuelan Gu, Shanghai (CN); Yanling Liu, Shanghai (CN); Fengjuan Tu, Shanghai (CN)

(73) Assignee: CONOPCO, INC., Englewood Cliffs, NJ (US)

(*) Notice: Subject to any disclaimer, the term of this patent is extended or adjusted under 35 U.S.C. 154(b) by 0 days.

(21) Appl. No.: 17/262,250

(22) PCT Filed: Jul. 8, 2019

(86) PCT No.: PCT/EP2019/068237
§ 371 (c)(1),
(2) Date: Jan. 22, 2021

(87) PCT Pub. No.: WO2020/025257
PCT Pub. Date: Feb. 6, 2020

(65) Prior Publication Data

US 2021/0346274 A1 Nov. 11, 2021

(30) Foreign Application Priority Data

Jul. 30, 2018 (WO) ................ PCT/CN2018/097728
Aug. 31, 2018 (EP) .................................... 18191914

(51) Int. Cl.

| | |
|---|---|
| ***A61K 8/9789*** | (2017.01) |
| ***A61K 8/9728*** | (2017.01) |
| ***A61K 8/34*** | (2006.01) |
| ***A61K 8/35*** | (2006.01) |
| ***A61K 8/49*** | (2006.01) |
| ***A61K 8/60*** | (2006.01) |
| ***A61K 8/63*** | (2006.01) |
| ***A61K 8/67*** | (2006.01) |
| ***A61Q 17/04*** | (2006.01) |
| ***A61Q 19/02*** | (2006.01) |

(52) U.S. Cl.
CPC ............ *A61K 8/9789* (2017.08); *A61K 8/347* (2013.01); *A61K 8/35* (2013.01); *A61K 8/498* (2013.01); *A61K 8/4926* (2013.01); *A61K 8/4973* (2013.01); *A61K 8/602* (2013.01); *A61K 8/63* (2013.01); *A61K 8/675* (2013.01); *A61K 8/9728* (2017.08); *A61Q 17/04* (2013.01); *A61Q 19/02* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 2002/0160059 | A1 | 10/2002 | Xiao |
| 2003/0026823 | A1 | 2/2003 | Fried et al. |
| 2005/0136139 | A1 | 6/2005 | Kruse et al. |
| 2005/0158259 | A1 | 7/2005 | Kropke et al. |
| 2005/0191266 | A1 | 9/2005 | Raschke et al. |
| 2007/0110835 | A1 | 5/2007 | Maes et al. |
| 2007/0196289 | A1 | 8/2007 | Blatt et al. |
| 2011/0236509 | A1 | 9/2011 | Chakrabortty et al. |
| 2012/0136067 | A1 | 5/2012 | Ruppert et al. |

(Continued)

FOREIGN PATENT DOCUMENTS

| | | |
|---|---|---|
| CN | 102836098 | 12/2012 |
| CN | 106852768 | 6/2017 |
| CN | 106852795 | 6/2017 |

(Continued)

OTHER PUBLICATIONS

Search Report and Written Opinion in EP18191914; dated Nov. 22, 2018; European Patent Office (EPO).

(Continued)

*Primary Examiner* — Nannette Holloman
(74) *Attorney, Agent, or Firm* — Stephanie Huang

(57) ABSTRACT

Disclosed is a composition comprising a plurality of active botanical ingredients, each predominantly associated with an in-use beneficial effect on an animate or inanimate substrate, where said composition comprises: (i) a first aqueous extract of a material derived from a first plant, said first extract comprising a first amount of a first active botanical ingredient; (ii) a second aqueous extract of a material derived from a second plant whose genus is not the same as the first plant, said second extract comprising a first amount of a second active botanical ingredient; (iii) an additional amount of said first active botanical ingredient; and (iv) an additional amount of said second active botanical ingredient; where each said additional amount is included by spiking said composition or the corresponding aqueous extract selectively with said first and said second active botanical ingredients, such that ratio of said first amount of said first active botanical ingredient to its corresponding additional amount and ratio of said first amount of said second active botanical ingredient to its corresponding additional amount in the composition is from 1:1 to 1:3000 parts by weight, wherein said composition is substantially free of non-aqueous extracts of any material derived from said first or said second plant wherein said first plant is *Atractylodes macrocephala* and said first active botanical ingredient is atractylenolide I, II or III and further wherein said second plant is *Glycyrrhiza uralensis, Glycyrrhiza inflata* or *Glycyrrhiza glabra* and said second active botanical ingredient is licochalcone A or glabridin.

12 Claims, No Drawings

(56) References Cited

U.S. PATENT DOCUMENTS

| | | | |
|---|---|---|---|
| 2014/0161898 | A1 | 6/2014 | Collins et al. |
| 2014/0242013 | A1 | 8/2014 | Yu et al. |

FOREIGN PATENT DOCUMENTS

| | | |
|---|---|---|
| CN | 106852898 | 6/2017 |
| CN | 106860160 | 6/2017 |
| CN | 106860304 | 6/2017 |
| CN | 106860309 | 6/2017 |
| CN | 106860325 | 6/2017 |
| CN | 106860343 | 6/2017 |
| CN | 107595756 | 1/2018 |
| EP | 1537849 | 6/2005 |
| EP | 1839645 | 10/2007 |
| EP | 2080436 | 7/2009 |
| EP | 2520182 | 11/2012 |
| JP | 2012077003 | 4/2012 |
| WO | WO2013002191 | 1/2013 |
| WO | WO2014173635 | 10/2014 |

OTHER PUBLICATIONS

Search Report and Written Opinion in PCTEP2019068237; dated Aug. 12, 2019; World Intellectual Property Org. (WIPO).

IPRP2 in PCTEP2019068237; dated Oct. 20, 2020; World Intellectual Property Org. (WIPO).

Written Opinion 2 in PCTEP2019068237; dated Jun. 12, 2020; World Intellectual Property Org. (WIPO).

Yan Ye et al.; Involvement of p38 MAPK signaling pathway in the anti-melanogenic effect of San-bai-tang, a Chinese herbal formula, in B16 cells; Journal of Ethnopharmacology; Sep. 15, 2010; pp. 533-535 vol. 132; Elsevier.

GNPD Mintel; Gluta White Bar Soap; Bright Star; Feb. 2018; pp. 1-2, Record ID 5431943; Thailand.

GNPD Mintel; Emulsion; Stime Ferment Whitening; Feb. 2016; pp. 1-2, Record ID 3830213; China.

GNPD Mintel; Secret Whitening Moisture Face Cream; Pacare Bessie Le'SKIN; Jan. 2016; pp. 1-2, Record ID 3700201; Thailand.

GNPD Mintel; Lamild Baby Hair Serum; ai+aoon Baby; Sep. 2016; pp. 1-2, Record ID 4264117; Thailand.

GNPD Mintel; Loose Powder; Boots Botanies Whitening; Dec. 2015; pp. 1-2, Record ID 3661579; Thailand.

Vengerovsky A.I.; Pharmacological incompatibility; Bulletin of Siberian Medicine; 2003; PP49-56, with english translation; vol. 3; Russian Federation.

D.A. Muravjeva; Pharmacognosy (with herb biochemistry fundamentals): Manual; Meditsina; 1978 PP23, 61 with english translation; Russian Federation.

Jianmin Chen et al.; Inhibitory mechanisms of glabridin on tyrosinase; Spectrochimica Acta Part A Molecular and Biomolecular Spectroscopy; 2016; pp. 111-117; vol. 168; Elsevier.

COMPOSITIONS COMPRISING ACTIVE BOTANICAL INGREDIENTS

CROSS REFERENCE TO RELATED APPLICATIONS

The present application is a U.S. National Phase Application under 35 U.S.C. § 371 of International Application No. PCT/EP2019/068237, filed on Jul. 8, 2019, which claims priority to International Application No. PCT/CN2018/097728, filed on Jul. 30, 2018, and European Patent Application No. 18191914.3, filed on Aug. 31, 2018, the contents of which are incorporated herein in their entireties.

FIELD OF THE INVENTION

The present invention relates to compositions comprising a combination of active botanical ingredients, particularly to cosmetic compositions.

BACKGROUND OF THE INVENTION

Traditional systems of medicine have existed for centuries. Traditional Chinese Medicine and Ayurvedic preparations have remained popular due to their proven in-use benefits. A variety of compositions including foods, refreshment and cosmetic compositions contain extracts or portions of plant-based materials where the underlying knowledge is derived from traditional systems of medicine.

Cosmetic compositions often contain one or more active botanical ingredients which are extracted from e.g., roots, stem, fruits, leaves or flowers of plants. Usually the extracts are aqueous extracts. The reasons for widespread use of aqueous extracts is efficacy and consumer safety. Usually an extract contains a plurality of active ingredients of which only some are efficacious and are associated with one or more in-use benefits. Such extracts often also contain other ingredients which may be not be associated with any in-use benefits. In some cases, such other ingredients may have an effect which is antagonistic to the effect of the beneficial active ingredients. Further, some other ingredients may play a supporting role; helping the active ingredient(s) perform its part. As there are a plurality of chemicals in an extract and at present the composition and mode of action of all such chemical ingredients may not be fully understood, the present inventors presume that every ingredient in the aqueous extract plays a role but there is at least one ingredient which is primarily associated with an in-use benefit.

Aqueous extracts have their own limitations because only a fraction of the active ingredient usually gets extracted (from the plant material) and the extracts may usually contain substantial amount of non-beneficial fractions like non-saponifiable matter, gums and resins. If a formulation scientist intends to include a higher amount of any active ingredient in given composition, intended for use by a consumer, the easier option is to up-dose or increase the quantity of the extract in the composition. Another option is to pre-treat the plant material, for example by pounding or grinding the roots or the bark.

Usually aqueous extracts contain minute quantities of the beneficial active ingredients, and in some cases the amount could be as low as few milligrams per kilogram or per litre of the extract. Limitations of processing conditions and equipment have left practically little room for process engineers to extract more of the ingredients from the plant-based materials. In addition, there is a risk of causing denaturization of the active ingredients if conditions such as pressure or temperature are altered significantly without understanding the implications. In an aqueous extract usually the active ingredient(s), the non-active ingredients, the antagonistic ingredient(s), if any, and the supporting ingredients are all present in definite ratios with respect to each other.

If there is need to increase or enhance the amount of an active botanical ingredient in the concerned composition, an easier approach is to change the solvent from water to a non-aqueous solvent, such as alcohols, especially ethanol, and thereby get a non-aqueous extract of the same plant-based material. Non-aqueous solvents are generally considered to be more potent solvents. However, when such a solvent is used, the usual observation is that the amount of every ingredient increases in the extract vis-a-vis the corresponding aqueous extract. In other words, although the absolute amount of the active ingredient(s) may increase, the relative amount of such ingredient(s), in relation to other ingredients, remains the same. An additional problem with non-aqueous solvents is that some non-extractible material (not extractable by using water) might also get extracted by such solvents and it might pose a risk to consumers or could manifest itself in the form of an unwanted colour or an unwanted in-use side effect.

Generally, such compositions have a combination of two or more active botanical ingredients as it is believed in several cases (and also proven in some cases) that such active botanical ingredients derived from different plants or herbs have synergistic in-use benefit.

US20140242013 A1 (Hong Kong Baptist University) discloses a Chinese medicinal formula comprising Atractylodis Macrocephalae Rhizoma, Glycyrrhizae Radix et Rhizoma, Angelicae sinensis Radix, Paeoniae Radix Alba and Poria for skin care. It further relates to a method for preparing bioactive fraction of this formula and to the applications of the bioactive fraction in skin-whitening and anti-skin-aging. The blended herbal formula is soaked with 250 mL distilled water for 1 hour, extracted under reflux for 4 hours and then filtered to obtain a first herbal extract. The herbal residuals of the first extract are further reflux-extracted with 8-, followed by 5-fold volume (y/w) of distilled water for 2 hours and 1 hour to obtain the second and third herbal extracts, respectively. The second and third extracts are combined with the first herbal extract to form a combined extract. The combined extract is concentrated under reduced pressure to a suitable volume (about 25 ml) to form a concentrated extract which, after undergoing some more steps, is used in the cosmetic compositions.

US 2003/026823 (FRIED HOWARD ET AL) discloses compositions for use in repelling insects that are inexpensive to manufacture, easily applied and/or integrated and non-injurious to plant and animal life, including citronella oil, geranium oil, rosemary oil, peppermint oil, D-limonene, aldehyde C-14 and aldehyde C-18. Preferred compositions additionally contain lavender oil, piperitone, and eucalyptus oil.

CN 106 852 795 (CHANGSHA XIEHAQJI BIOLOGY ENG CO LTD) discloses a preparation method of a freckle-removing emulsion. The freckle-removing emulsion is prepared by mixing of phytosterol, glabridin, a lithospermum extracted liquid, a purslane extracted liquid, a garden balsam stem extracted liquid, paeonol, a licorice flavonoid liquid, dipotassium glycyrrhizinate, a magnolin extracted liquid, a chamomile extracted liquid, arbutin, a cactus extract, an aloe extracted liquid, an Inonotus obliquus extract, a honeysuckle extracted liquid, a Platycladus orientalis extracted liquid, an arnica extracted liquid, a dandelion extracted liquid, a licorice extracted liquid, a Salvia Miltiorrhiza extracted liquid, a grape seed extracted liquid, a folium artemisiae argyi extracted liquid, a bighead atractylodes rhizome extracted liquid, a Gynostemma pentaphyllum extracted liquid, a Gentiana scabra Bunge extracted liquid, a garden burnet extracted liquid, a saussurea involucrata extracted liquid, emulsifying wax, polyglutamic acid, essence, and ionized water.

CN 107 595 756 (JIANG BINGBING) discloses a whitening black-removing compound which contains the following components by weight percent: 1-10 percent of nicotinamide, 1-5 percent of licochalcone A, 1-10 percent of arbutin, 0.5-1.5 percent of bletilla root extract, 0.5-1.5 percent of atractylodes root extract, 0.05-0.3 percent of pearl extract, 0.05-0.3 percent of ginseng extract, 0.01-0.5 percent of nymphaea alba flower, 0.01-0.5 percent of ligusticum root, 20-40 percent of glyceroland the balance of water CN106 860 325 (CHANGSHA XI EHAQJI BIOLOGY ENG CO LTD) discloses a ferment freckle-removal toner. As disclosed, the ferment freckle-removal toner is prepared by mixing phytosterin, glabridin, a gromwell extracting solution, vitamin D3, lipase, Lactobacillus plantarum, a licorice root flavone solution, dipotassium glycyrrhetate, a magnolin extracting solution, a camomile extracting solution, arbutin, a cereus extract, an aloe extracting solution, an Inonotus obliquus extract, a honeysuckle flower extracting solution, a Platycladus orientalis extracting solution, a mountain tobacco extracting solution, a taraxacum extracting solution, a licorice root extracting solution, a propolis extracting solution, an eyebright extracting solution, rose hydrosol, a glabrous greenbrier rhizome extracting solution, a witch hazel extracting solution, a gentian extracting solution, a Sanguisorba officinalis extracting solution, a clove extracting solution, isopropyl myristate, polyglutamic acid, fragrance and ionized water.

US20120136067 A1 (Beiersdorf, 2003) discloses the use of a UV filter combination of a) 2-ethylhexyl 2-cyano-3,3-diphenylacrylate (INCI: octocrylene), b) 4-(tert-butyl)-4'-methoxydibenzoylmethane (INCI: butyl methoxydibenzoyl methane) to increase the storage stability of licochalcone A or licorice extracts in cosmetic O/W emulsions.

US2005191266 A1 (Beiersdorf, 2003) discloses cosmetic or dermatological preparation which comprises an effective amount of at least one of licochalcone A and an extract of radix glycyrrhizae inflatae that comprises licochalcone A.

US2011236509A (Unilever) discloses topical composition and a method for reducing or preventing occurrence of acne on the skin. An object of the invention is to provide for a combination of herbal extracts that interact synergistically to provide a cosmetic composition for prevention, reduction or treatment of acne. The composition comprises an extract of a first active which is Azhadirachta indica; and (ii) an extract of a second active selected from Momordica charantia or Sesamum indicum.

WO14173635 A1 (Unilever) discloses a topical composition for hair growth comprising synergistic combination of extracts of plant source. The composition not only retains hair bulb in the anagen state longer but also ensures longer hair. This is achieved through a combination of a gallic acid ester and an extract of Glycyrrhiza glabra or Sesamum indicum which is applied on the hair or scalp.

One of the objects of this invention is to provide an efficacious composition, in so far as its in-use benefit on an animate or inanimate substrate is concerned, where the composition comprises a combination of botanical active ingredients extracted from the corresponding plant material, such as roots or bark.

SUMMARY OF THE INVENTION

The problems have been solved by way of the compositions in accordance with the invention.

In accordance with a first aspect of the invention, disclosed is a composition comprising a plurality of active botanical ingredients, each predominantly associated with an in-use beneficial effect on an animate or inanimate substrate, where said composition comprises:

(i) a first aqueous extract of a material derived from a first plant, said first extract comprising a first amount of a first active botanical ingredient;

(ii) a second aqueous extract of a material derived from a second plant whose genus is not the same as the first plant, said second extract comprising a first amount of a second active botanical ingredient;

(iii) an additional amount of said first active botanical ingredient; and (iv) an additional amount of said second active botanical ingredient;

where each said additional amount is included by spiking said composition or the corresponding aqueous extract selectively with said first and said second active botanical ingredients, such that ratio of said first amount of said first active botanical ingredient to its corresponding additional amount and ratio of said first amount of said second active botanical ingredient to its corresponding additional amount in the composition is from 1:1 to 1:3000 parts by weight, wherein said composition is substantially free of non-aqueous extracts of any material derived from said first or said second plants, wherein said first plant is *Atractylodes macrocephala* and said first active botanical ingredient is atractylenolide I, II or III and further wherein said second plant is *Glycyrrhiza uralensis, Glycyrrhiza inflata* or *Glycyrrhiza glabra* and said second active botanical ingredient is licochalcone A or glabridin.

In accordance with a second aspect of the invention, disclosed is a composition comprising a plurality of active botanical ingredients, each predominantly associated with an in-use beneficial effect on an animate or inanimate substrate, where said composition comprises:

(i) an aqueous co-extract of a material derived from a first plant and a material derived from a second plant whose genus is not the same as the first plant, said aqueous extract comprising a first amount of a first active botanical ingredient originating from said first plant and a second active botanical ingredient originating from said second plant;

(ii) an additional amount of said first active botanical ingredient; and (iii) an additional amount of said second active botanical ingredient;

where each said additional spiked amount is included by spiking said composition or the aqueous co-extract selectively with said first and said second active botanical ingredients, such that ratio of said first amount of said first active botanical ingredient to its corresponding additional amount in the composition and ratio of said first amount of said second active botanical ingredient to its corresponding additional amount in the composition is from 1:1 to 1:3000 parts by weight, wherein said composition is substantially free of non-aqueous extracts of any material derived from said first or said second plant, wherein said first plant is *Atractylodes macrocephala* and said first active botanical ingredient is atractylenolide I, II or III and further wherein said second plant is *Glycyrrhiza uralensis, Glycyrrhiza inflate* or *Glycyrrhiza glabra* and said second active botanical ingredient is licochalcone A or glabridin.

These and other aspects of the invention will hereinafter be described in detail.

DETAILED DESCRIPTION OF THE INVENTION

For the avoidance of doubt, any feature of one aspect of the present invention may be utilized in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description and claims indicating amounts of material or conditions of reaction, physical properties of materials and/or use are to be understood as modified by the word "about". Numerical ranges expressed in the format "from x to y" are understood to include x and y. In specifying any range of values or amounts, any particular upper value or amount can be associated with any particular lower value or amount.

As used herein, the indefinite article "a" or "an" and its corresponding definite article "the" means at least one, or one or more, unless specified otherwise. The various features of the present invention referred to in individual sections above apply, as appropriate, to other sections mutatis mutandis. Consequently, features specified in one section may be combined with features specified in other sections as appropriate. Any section headings are added for convenience only, and are not intended to limit the disclosure in any way.

The term active botanical ingredient means an ingredient present in the aqueous extract and which is predominantly associated with at least one in-use beneficial effect. For example, licochalcone A or glabridin are active botanical ingredients present in the aqueous extract of *Glycyrrhiza glabra* and these ingredients are predominantly associated with skin lightening or reduction of melanin content of a pigmented skin.

The expression "associated with" means that the ingredient is largely responsible for causing the in-use beneficial effect or known for causing the effect.

The expression "in-use beneficial effect" means any perceivable effect which could either be perceived by the senses or could be measured by any known method using any known device or machine. For example, in the case of licochalcone A or glabridin as active botanical ingredients present in the aqueous extract of *Glycyrrhiza glabra*; skin lightening or reduction of melanin content of a pigmented skin are the in-use beneficial effects.

The term inanimate substrates include hard surfaces found in and around a house e.g. wooden, metal, ceramic, glass and paint surfaces, ceramic, vitrified tile, paper, polystyrene or marble or soft surfaces such as clothing, carpets, curtains and other textiles. Animate substrate implies those substrates which are other than inanimate substrate and could be human or animal body, more preferably human body, i.e. human skin, hair, teeth or underarms. For the purposes of this invention animate substrates do not include plant surfaces.

The term aqueous extract means that the extract is obtained only by using water as the solvent for extraction. In one aspect the extract per se is in solid form such as a powder or granules with some amount of moisture in it. The term aqueous extract does not mean that the extract necessarily contains a substantial amount of water. Alternatively, the extract per se is in aqueous form comprising the non-active botanical ingredient and the active botanical ingredient. In this case, the extract does contain a substantial amount of water.

The term non-active botanical ingredient means an ingredient which is present in the aqueous extract and which is predominantly not associated with an in-use beneficial effect. Alternatively, the term means an ingredient which is present in the aqueous extract and which is predominantly associated with an in-use beneficial effect which is other than the effect with which the active botanical ingredient is associated with.

The expression, set of non-active botanical ingredients, means the presence of at least two non-active botanical ingredients.

The term plant for the purpose of this invention includes angiosperms, gymnosperms, bryophytes, pteridophytes and fungi.

The expression, material derived from a plant means a part of the plant such as root, leaves, stem, fruits, flowers or bark. Where the plant is a fungus, such as mushroom, then the material is preferably derived from the sclerotium. Such a material could be directly sourced from the plant or it could also have undergone a pre-processing step such as washing, pounding or pulverization. Further, such a material could also be a material obtained from the plant such as a gum, exudate or latex.

The expression non-aqueous extract means that the extract is obtained by using a solvent other than water. It is preferred that the non-aqueous extract means alcoholic extract, especially ethanolic extract.

The Compositions of The Invention

Compositions in accordance with the invention comprise a plurality of active botanical ingredients, each predominantly associated with at least one in-use beneficial effect on an animate or inanimate substrate.

In one aspect the composition in accordance with the invention is a detergent composition, a fabric conditioner or a hard-surface cleaning composition and the beneficial effect is on an inanimate substrate Alternatively, the composition of the invention is a cosmetic, a food product, a beverage, an ice-cream or a frozen desert and the beneficial effect is on an animate substrate It is preferred that the composition in accordance with the invention is a cosmetic composition and the in-use beneficial effect is a cosmetic effect. The term cosmetic effect is variable and could have various meanings depending on the nature and purpose of the composition. For example, when the cosmetic composition is a shampoo, the cosmetic effect could be shinier hair, fizz-free hair or straighter or more manageable hair. When the cosmetic composition is a deodorant or antiperspirant the corresponding cosmetic effect is reduced perspiration.

Preferably the cosmetic composition is a skin care composition, a skin cleansing composition, a deodorant, an antiperspirant, a hair care composition or an oral care composition. Hair care compositions include shampoo, hair conditioner, hair cream, hair gel, hair oil, hair serum and hair colour. Skin care compositions include creams, gels, lotions, wipes, foundation, cosmetic masks, mascara, lipstick and after-shave preparations. Oral care compositions include toothpaste and mouthwash.

As used herein, the term "food" or "food products" includes dairy products (including milk and yoghurts), desserts, convenience foods/snacks, breakfast cereals and cereal bars, mayonnaises, dressings, sandwich fillings, ready-cook meals, bread, soups, noodles, biscuits and cakes. Beverages, ice-cream and frozen desserts are included under refreshment. The term refreshment includes frozen confections such as ice creams, water ices and sorbets and yoghurt ice creams. Suitable beverages include tea, tea-flavoured drinks, soy based products, coffee, soft drinks (e.g. carbonated squashes) and fruit juice.

Preferably, the food composition further includes at least one of protein, carbohydrate or fat. It is especially preferred that the food composition includes at least protein and carbohydrate. Alternatively, a source of one of protein, carbohydrate and/or fat can be given as the same time as the food composition, for example, if the food composition does not contain substantial amounts of these ingredients.

Suitable sources of protein include dairy sources such as milk, yoghurt, kefir, cheese, or cream. Other animal sources may also be used depending upon the type of food composition. Alternatively, the food composition may include vegetable derived proteins such as soy-protein, rice protein, pea protein or wheat protein.

The amounts of protein, fat, carbohydrate and other ingredients in the food or refreshment composition will vary according to the product format and the applicable national or regional legislations.

The compositions in accordance with the invention comprise a first aqueous extract and a second aqueous extract. The contents of the aqueous extracts depend on the plant and the material derived from the concerned plant. For example, the constitution or composition of ingredients in aqueous extract of the roots of a plant may not be the same as the composition of ingredients in aqueous extract of the bark of the same plant. The first amount is that amount which is inherently present in the extract as being present in the concerned material and being extractable therefrom under standard conditions of extraction.

The first aqueous extract is of a material derived from a first plant. The first aqueous extract comprises a first amount of a first active botanical ingredient.

The first plant is *Atractylodes macrocephala* and the first active botanical ingredient is atractylenolide I, II or III.

The compositions of the invention comprise a second aqueous extract of a material derived from a second plant whose genus is not the same as the first plant, said second extract comprising a first amount of a second active botanical ingredient. The first amount is that amount which is inherently present in the extract as being present in the concerned material and being extractable therefrom under standard conditions of extraction.

The second plant is *Glycyrrhiza uralensis* or *Glycyrrhiza inflate*, or *Glycyrrhiza glabra* and said second active botanical ingredient is licochalcone A or glabridin.

The compositions of the invention further comprise an additional amount of the first active botanical ingredient. The compositions of the invention further comprise an additional amount of the second active botanical ingredient. The additional amount is over and above the amount already present in the extract and referred to as the first amount and second amount respectively. As the name suggests, the additional amount is included by selectively spiking the composition or the corresponding aqueous extract with said first and said second active botanical ingredient. Preferably the additional amount is included by spiking the corresponding aqueous extract.

The ratio of the first amount of said first active botanical ingredient to its corresponding additional amount and ratio of said first amount of said second active botanical ingredient to its corresponding additional amount in the composition is from 1:1 to 1:3000 parts by weight. More preferably this ratio is 1:1 to 1:2500 parts by weight. The wide range of the ratio indicates the formulation flexibility concerning the applicable first amount and the corresponding additional amount is concerned. Such a wide formulation flexibility is necessary because in some cases, in view of inherently less amount of the active botanical ingredient in the material derived from the first (or the second) plant or both, or in view of restrictions/complexity involved in extraction process, the concerned first amount in the concerned aqueous extract is bound to be low and sometimes even 0.00001 wt % based on the extract. In such a case, when the extract is to be used in the composition, for example a cosmetic composition like a fairness cream, the maximum possible amount of the active that can be dosed or included in the composition is also bound to be extremely low. The reason is that to up-dose the amount of the active, the formulation scientist would need to up-dose the amount of the concerned extract and that might not be technically or commercially feasible. Therefore, in such a case, the formulation scientist would have a wide-ranging discretion, based on their knowledge of the principles of formulations, to include a higher amount of the concerned additional amount, for example, at a ratio of 1:2000 parts by weight.

On the other hand, if the inherent, or the first amount of the concerned active botanical ingredient is already high enough or sufficiently high in the concerned first or second extract, then the formulation scientist might have no reason to include a higher amount of the concerned additional amount, for example, at a ratio of 1:2000 parts by weight. In such a case, the scientist might prefer the ratio of 1:1 or 1:2 parts by weight.

The compositions of the invention are substantially free of non-aqueous extract of any material derived from said first or said second plant. Preferably the term non-aqueous extract means alcoholic extract, especially ethanolic extract. The reason, as already described hereinbefore is that non-aqueous extracts often contain unwanted ingredients or that they often have other interfering ingredients that may pose a consumer-relevant problem like an unwanted colour or odour to the concerned composition.

It is preferred that the first amount of the first active botanical ingredient and said first amount of said second active botanical ingredient is 0.00001 wt % to 5 wt % by weight of the composition. More preferably this amount is 0.001 wt % to 4 wt % by weight of the composition. Still more preferably it is 0.001 wt % to 2 wt % by weight of the composition. As this is the actual amount of the active botanical ingredient in the compositions of the invention, the formulation scientists need to add the corresponding amount of the concerned extract (by doing calculations) such that the composition ultimately would have the requisite amount of the concerned active botanical ingredient.

Further preferably, in the compositions of the invention, each said additional spiked amount is 0.00001 wt % to 10 wt % by weight of said composition.

It is preferred that when the first plant is Atractylodes macrocephala and the first active botanical ingredient is atractylenolide I, II or III and when the second plant is *Glycyrrhiza uralensis* (or *Glycyrrhiza inflate* or *Glycyrrhiza*

*glabra*) and the second active botanical ingredient is licochalcone A or glabridin, the composition of invention is a cosmetic composition and the beneficial effect is skin lightening, as indicated by down regulation of expression of melanin in a pigmented model human living skin-equivalent.

Further preferably the compositions of the invention comprise another (i.e., a third) aqueous extract of a material derived from a third plant whose genus is not the same as the first or the second plant, where said another extract comprises a first amount of a third active botanical ingredient and an additional amount of said third active botanical ingredient included by spiking said composition or the corresponding aqueous extract selectively with said third active botanical ingredient, such that ratio of said first amount of said third active botanical ingredient to its corresponding additional amount in said composition is from 1:1 to 1:3000 parts by weight, more preferably this ratio is 1:1 to 1:2500 parts by weight. In such cases also, the composition is substantially free of non-aqueous extract of any material derived from said third plant.

Preferably the third plant is Paeonia lactiflora and said third active ingredient is paeoniflorin.

Yet further preferably the compositions of the invention comprise another (i.e., a fourth) aqueous extract which is of a material derived from a fourth plant whose genus is not the same as the first, second or third plant, where said fourth extract comprises a first amount of a fourth active botanical ingredient and an additional amount of said fourth active botanical ingredient included by spiking said composition or the corresponding aqueous extract selectively with said fourth active botanical ingredient, such that ratio of the first amount of said fourth active botanical ingredient to its corresponding additional amount in said composition is from 1:1 to 1:3000 parts by weight, wherein said composition is substantially free of non-aqueous extract of any material derived from the fourth plant.

Preferably the fourth plant is Poria cocos and the fourth active ingredient is pachymic acid. This plant is a fungus, a mushroom. The material is derived from its sclerotium.

In accordance with a second aspect of the invention, disclosed is a composition comprising a plurality of active botanical ingredients, each predominantly associated with at least one in-use beneficial effect on an animate or inanimate substrate, where said composition comprises:

(i) an aqueous co-extract of a material derived from a first plant and a material derived from a second plant whose genus is not the same as the first plant, said aqueous extract comprising a first amount of a first active botanical ingredient originating from said first plant and a first amount of a second active botanical ingredient originating from said second plant;

(ii) an additional amount of said first active botanical ingredient; and (iii) an additional amount of said second active botanical ingredient;

where each said additional amount is included by spiking said composition or the aqueous co-extract selectively with said first and said second active botanical ingredients, such that ratio of said first amount of said first active botanical ingredient to its corresponding additional amount in the composition and ratio of said first amount of said second active botanical ingredient to its corresponding additional amount in the composition is from 1:1 to 1:3000 parts by weight, wherein said composition is substantially free of non-aqueous extracts of any material derived from said first or said second plants wherein said first plant is *Atractylodes macrocephala* and said first active botanical ingredient is atractylenolide I, II or III and further wherein said second plant is *Glycyrrhiza uralensis, Glycyrrhiza inflata* or *Glycyrrhiza glabra* and said second active botanical ingredient is licochalcone A or glabrid in.

The difference between this and the first aspect of the invention is that this aspect pertains to an aqueous co-extract of a material derived from a first plant and a material derived from a second plant whose genus is not the same as the first plant, whereas in the first aspect, reference is made to individual extracts of a material derived from a first plant and a material derived from a second plant. The term “co-extract” means that said first plant and second plant are exacted together in an aqueous medium. This is in principle different from the first aspect wherein the first plant and second plant have been extracted separately followed by combination of those extract to obtain the composition as per the present invention.

In the compositions according to the second aspect of the invention it is preferred that the compositions comprise another aqueous extract of a material derived from a third plant whose genus is not the same as the first or the second plant, where said another extract comprises a first amount of a third active botanical ingredient and an additional amount of said third active botanical ingredient included by spiking said composition or the corresponding aqueous extract selectively with said third active botanical ingredient, such that ratio of said first amount of said third active botanical ingredient to its corresponding additional amount in said composition is from 1:1 to 1:3000 parts by weight, more preferably this ratio is 1:1 to 1:2500 parts by weight. In such cases also, the composition is substantially free of non-aqueous extract of any material derived from said third plant. It is preferred that in the co-extraction process, use is made of the material derived from the third plant so that the extract comprises or subsumes the another extract referred to hereinabove.

Preferably the third plant is Paeonia lactiflora and said third active ingredient is paeoniflorin.

Yet further preferably in the compositions according to the second aspect of the invention it is preferred that the compositions comprise another (i.e., a fourth) aqueous extract which is of a material derived from a fourth plant whose genus is not the same as the first, second or third plant, where said fourth extract comprises a first amount of a fourth active botanical ingredient and an additional amount of said fourth active botanical ingredient included by spiking said composition or the corresponding aqueous extract selectively with said fourth active botanical ingredient, such that ratio of the first amount of said fourth active botanical ingredient to its corresponding additional amount in said composition is from 1:1 to 1:3000 parts by weight, wherein said composition is substantially free of non-aqueous extract of any material derived from the fourth plant. It is preferred that in the co-extraction process, use is made of the material derived from the fourth plant so that the extract comprises or subsumes the another extract referred to hereinabove.

Preferably the fourth plant is Poria cocos and the fourth active ingredient is pachymic acid. This plant is a fungus, a mushroom. The material is derived from its sclerotium.

The Compositions

The composition in accordance with this invention is a detergent composition, a fabric conditioner or a hard-surface cleaning composition and said in-use beneficial effect is on an inanimate substrate. The inanimate substrate could, for example, be fabric or a hard surface like ceramics and tiles.

Alternatively, the composition in accordance with the invention is a cosmetic, a food product, a beverage, an ice-cream or a frozen desert and said in-use beneficial effect is on an animate substrate When the composition in accordance with the invention is a cosmetic composition, the in-use beneficial effect is a cosmetic effect. The cosmetic effect could vary depending on the nature and purpose of the cosmetic composition. Non-limiting examples thereof include skin lightening, skin whitening, amelioration of fine lines and wrinkles, blurring of surface defects, hair straightening, hair conditioning, antiperspirant effect, deodorant effect and moisturization of skin.

Cosmetic composition as used herein, is meant to include a composition for topical application to skin of mammals, especially humans. Such a composition may be generally classified as leave-on or rinse off, and includes any product applied to a human body for improving appearance, cleansing, odor control or general aesthetics. The personal care composition is preferably a leave-on composition. The composition of the present invention can be in the form of a liquid, lotion, cream, foam, scrub, gel, soap bar or toner, or applied with an implement or via a face mask, pad or patch. Non-limiting examples of personal care compositions include leave-on skin lotions and creams, shampoos, conditioners, shower gels, toilet bars, antiperspirants, deodorants, depilatories, lipsticks, foundations, mascara, sunless tanners and sunscreen lotions. Thus the preferred cosmetically acceptable base is an emulsion, lotion, cream, foam, gel, soap bar, stick, mask, pad or patch. Preferred cosmetically acceptable base in leave-on compositions are an emulsion, lotion, cream, foam, gel or stick. “Skin” as used herein is meant to include skin on the face and body (e.g., neck, chest, back, arms, underarms, hands, legs, buttocks and scalp).

When the composition of the invention is a cosmetic composition, preferably it comprises a cosmetically acceptable base. The cosmetically acceptable base is preferably a cream, lotion, gel or emulsion base. Such compositions may be prepared using different cosmetically acceptable emulsifying or non-emulsifying systems and vehicles. Preferred cosmetically acceptable bases comprise 1 to 25% fatty acid, by weight of the composition. Further preferably the base comprises 0.1 to 10% soap by weight of the composition. A highly suitable base is a cream. Vanishing creams are especially preferred. Vanishing cream bases generally comprise 5 to 25% w/w fatty acid and 0.1 to 10% w/w soap. Vanishing cream base gives a highly appreciated matte feel to the skin. $C_{12}$ to $C_{20}$ fatty acids are especially preferred in vanishing cream bases, furthermore preferred being $C_{14}$ to $C_{18}$ fatty acids. The most preferred fatty acid is stearic acid. The fatty acid may also be a mixture of palmitic and stearic acid. Soap includes alkali metal salt of fatty acids, like sodium or potassium salts, most preferred being potassium stearate. Preferably such compositions comprise 0.1 to 10 wt %, more preferably 0.1 to 3 wt % soap.

The composition of the invention may comprise another skin lightening agents such as niacin, niacinamide, picolinamide, isonicotinamide or any other well-known skin lightening agent like 12-HSA, conjugated linoleic acid, kojic acid, arbutin or a resorcinol. Preferably, the composition of the invention comprises 0.1 to 10 wt %, more preferably 0.2 to 5 wt % skin lightening agent.

Preferably the cosmetic composition additionally comprises one or more inorganic or organic UV sunscreens. The more preferred organic sunscreens are 2-ethylhexyl-p-methoxycinnamate (as a UVB sunscreen agent) and/or butylmethoxydibenzoylmethane (as a UVA sunscreen agent). Preferably the composition comprises 0.1 wt % to 10 wt %, more preferably 0.1% to 5 wt %. Useful inorganic sunscreens include zinc oxide, iron oxide, silica, such as fumed silica, and titanium dioxide. Such particulate materials may further be coated with a hydrophobic agent.

The cosmetic composition of the invention may additionally comprise one or more emollient. Suitable emollients include stearyl alcohol, glycerol monoricinoleate, glycerol monostearate, mink oil, cetyl alcohol, isopropyl isostearate, stearic acid, isobutyl palmitate, isocetyl stearate, oleyl alcohol, isopropyl luarate, hexyl laurate, decyl oleate, octadecan-2-ol, isocetyl alcohol, eicosanylalcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, palm kernal oil, rapeseed oil, safflower seed oil, evening primrose oil, soybean oil, sunflower seed oil, avocado oil, olive oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate and myristyl myristate.

Such a composition preferably also comprises other diluents to facilitate their distribution when the composition is applied to the skin, such as liquid or solid emollients, solvents, humectants, thickeners and powders.

When the composition of the invention is a deodorant or an antiperspirant, it preferably comprises a conventional deodorant base as the carrier. By a deodorant is meant a product in the soft-solid, stick, gels, creams, and liquids in the form of roll-on, or in a propellant medium for topical/under-arm applications and such compositions may or may not contain anti-perspirant actives. The liquid carrier or mixture of carriers often constitutes from 30 to 95 wt % and in many instances from 40 to 80 wt % of the composition.

When the cosmetic composition according to the present invention is a hair care composition it includes a base preferably a dematologically/cosmetically acceptable base. The hair composition may suitably take the form of shampoos, conditioners, sprays, mousses, tonics, gels, oils, creams, air infused styling foams, rinses or lotions.

The choice of appropriate base will depend on the form of the hair composition and on whether the product formulated is meant to be left on the surface to which it is applied (e.g. hair spray, mousse, tonic, or gel), or rinsed off after use (e.g. shampoo, conditioner, rinses).

The base can be in a wide variety of forms. For example, it may be an oil-in-water, water-in-oil, water-in-oil-in-water, or oil-in-water-in-silicone emulsion. The dermatologically/cosmetically acceptable base used herein can include a wide range of components conventionally used in hair compositions. The base can be a solvent to dissolve or disperse the polymer of galacturonic acid and is preferably the C6 alcohols, lower alkyl acetate and mixtures thereof. The base can also contain a wide variety of additional materials such as acetone, hydrocarbons (such as isobutane, hexane, decene) and volatile silicon derivatives such as cyclomethicone. Depending on the type of composition, one or more additional ingredients may preferably be included in the compositions of the invention. Such additional ingredients include styling agents, such as resins and hair-setting polymers, perfumes, dyes, buffering or pH adjusting agents, viscosity modifiers, opacifiers, pearlescers, preservatives, antibacterial agents, antidandruff agents, foam boosters, proteins, moisturising agents, herb or other plant extracts and other natural ingredients.

The cosmetic compositions of the present invention may comprise a wide range of other optional components. The CTFA Cosmetic Ingredient Handbook, Second Edition, 1992, which is incorporated by reference herein in its entirety, describes a wide variety of non-limiting cosmetic and pharmaceutical ingredients commonly used in the skin care industry, which are preferably suitable for use in the compositions of the present invention. Examples include: antioxidants, binders, biological additives, buffering agents, colorants, thickeners, polymers, astringents, fragrance, humectants, opacifying agents, conditioners, exfoliating agents, pH adjusters, preservatives, natural extracts, essential oils, skin sensates, skin soothing agents, and skin healing agents.

When the topical composition according to the present invention is an oral care composition it includes a base, preferably an orally acceptable base. The orally acceptable base depends on the format in which the oral care composition is delivered. Most suitable formats are mouthwash, a toothpaste or a toothpowder. When the composition is formulated as a mouthwash, the orally acceptable base is water. A mouthwash preferably comprises 0.05 to 10 wt %, more preferably 0.05 to 8 wt %, most preferably 0.5 to 5 wt % of a surfactant. The surfactant is preferably cationic, anionic, or zwitterionic, most preferably cationic. When an anionic surfactant is present it is preferably chosen from alkali or alkaline earth metal salts of alkyl sulphonic acid, fatty acid, or alkyl ether sulphate. When a zwitterionic surfactant is present it is preferably chosen from betaines, sulphobetains, hydroxyl sulphobetains, or amino carboxylates. When a cationic surfactant is present it is preferably benzalkonium chloride, alkyl pyridinium chloride or quaternary ammonium gemini surfactants. The mouthwash composition of the invention is used for improving immunity either by using the composition with no dilution or after diluting the composition with water.

The oral care composition may be delivered in a toothpaste format. When the composition is a toothpaste, the orally acceptable base is an abrasive which may be calcium carbonate or abrasive silica. When calcium carbonate is the abrasive, the toothpaste is in an opaque paste format. An opaque toothpaste includes 15 to 70 wt % calcium carbonate, more preferably 30 to 60 wt %. Calcium carbonate (also known as chalk) is available in many forms and some of these forms are used in oral care compositions. Two commonly used forms are FGNC (fine ground natural chalk) and PCC (precipitated calcium carbonate). When abrasive silica is used, the toothpaste is usually delivered in a transparent gel format. The toothpaste preferably includes 2 to 15 wt % of a surfactant, preferably 2.2 to 10 wt %, more preferably 2.5 to 5 wt % of the composition. Preferred surfactants are anionic or amphoteric. The anionic surfactant is preferably an alkali metal alkyl sulphate, more preferably a sodium lauryl sulphate (SLS). Mixtures of anionic surfactants may also be employed. The amphoteric surfactant is preferably a betaine, more preferably an alkylamidopropyl betaine (wherein the alkyl group is a linear $C_{10}$ to $C_{18}$ chain), and most preferably is cocoamidopropyl betaine (CAPB). Mixtures of amphoteric surfactants may also be employed.

When the composition in accordance with the invention is a detergent composition. The laundry detergent composition may be a liquid, powder or gel. The laundry detergent composition is preferably a non-phosphate laundry composition, i.e., contains less than 1 wt % phosphate. Powder laundry detergent formulations are predominantly carbonate built, i.e. the weight percent of sodium carbonate is greater than the weight percent sum of other builder ingredients present. Preferably such compositions also comprise surfactants, polymers, enzymes, builders, shading dyes, bleaching agents, colour and perfumes.

When the composition of the invention is a hard surface cleaning composition, it preferably is dishwash composition or a floor cleaner. Dishwash compositions are available in various formats. These include powders, pastes, liquids and bars. Of all these formats, powders contain least amounts of surfactants while liquids contain the most. The total surfactant content is generally expressed as the total Active Detergent (AD) level. Powders are usually 2 to 4 AD products whereas dish wash or detergent liquids may be 5 to 30 AD products. In addition to surfactants which determine the AD level, such compositions also contain other additives like foam boosters, foam suppressants (or antifoam agents), hydrotropes, polymers, colour and perfume.

It is particularly preferred that the in-use beneficial effect of each said active botanical ingredient on said animate or inanimate substrate is same or similar. In such cases, formulation scientists could formulate better and more efficacious products in which the active botanical ingredients interact synergistically to provide a combined effect which is substantially more than the predictable mathematically additive effect.

The present invention also relates to a composition as per the present invention for use in skin lightening. In particular, use of the composition to reduce the melanin content of skin is contemplated.

The invention will now be explained with the help of non-limiting examples.

EXAMPLES

Example 1

An aqueous co-extract of the *Atractylodes macrocepbala* (root), *Paeonia lactiflora* (stem), *Poria cocos* (sclerotium) and *Glycyrrhiza glabra* (stem, bark) in the composition ratio of 2:2:2:1 parts by weight was prepared by the usual water-reflux process in which the duration of each reflux cycle was 30 minutes. There were two such cycles. A rotary evaporator maintained at 60° C. was used for vacuum distillation. The aqueous extract was freeze-dried into a powder. The extraction yield was 20:1 parts by weight.

Table 1 contains information about the amounts of the active botanical ingredients in the freeze-dried extract.

TABLE 1

| Ingredient | From the Plant | Amount/ppm |
|---|---|---|
| Atractylenolide I | *Atractylodes macrocephala* Koidz | 21.25 |
| Atractylenolide II | same | 93.21 |
| Atractylenolide III | same | 390.33 |
| Pachymic acid | *Poria cocos* | 4.29 |
| Albiflorin | *Paeonia lactiflora Pall* | 1588.87 |
| Paeoniflorin | same | 15143.22 |
| Ethyl gallate | same | 0.88 |
| Liquiritin | *Glycyrrhiza glabra* | 3113.52 |
| Isoliquiritigenin | same | 0.07 |
| Licochalcone A | same | 1.45 |
| Glabridin | same | 0.59 |

Example 2

Inhibition of Melanin in a Living Skin-Equivalent (LSE) Model

To determine whether the aqueous co-extract of Example 1 had any beneficial cosmetic effect on an animate surface (human skin), the extract was used in a test performed on a human living skin-equivalent. Details of the test are as follows:

Materials:

MelaKuits®, a reconstructed human pigmented LSE model, derived from 3D culture of normal human epidermal keratinocytes and melanocytes from Asian donors. It is available with Biocell (Xi'an, China).

The aqueous co-extract, was prepared as per Example 1.

Atractylenolide I, Glabridin and Koji acid were procured from commercial suppliers.

Method:

The pigmented LSE model was exposed to UVB (50 mJ/cm$^2$) for seven consecutive days day at periodic intervals of 24 hours to stimulate the synthesis of melanin. The extracts were applied topically on each LSE model on day 4 and day 6 with an interval of 48 hours for refreshing. For comparison, a blank experiment was carried out in which the LSE was neither exposed to UV radiation nor was any extract applied thereon. A control experiment was also carried out in which the LSE model was exposed to UV radiation, but no other treatment was followed.

On day 8, the appearance of each LSE model was assessed by photographing them. Thereafter, all the models subjected to the test were separated from their respective inserts and placed on a white plastic plate with the stratum corneum side facing up. The luminance (L*) value was read using a spectrophotometer CM700 (Konica-Minolta). For each model, the luminance was measured thrice, and the mean value was calculated for comparison.

The observations/data is summarised in Table 2.

TABLE 2

| Ref No. | Ingredient/conditions and amount | Melanin content# as % of control |
|---|---|---|
| 1 | Blank | 73.6 |
| 2 | Control | 100 |
| 3 | Kojic acid (positive control) 75 μM | 77.4 |
| 4 | Extract* of Example 1 50 μg/ml | 97.1 |
| 5 | Extract* of Example 1 100 μg/ml | 80.9 |
| 6 | Extract* of Example 1 300 μg/ml | 76.0 |
| 7 | AT-1 5 μM | 94.9 |
| 8 | Extract* of Example 1 50 μg/ml and AT-1 5 μM | 95.3 |
| 9 | Glabridin 2.5 μM | 97.1 |
| 10 | Extract* of Example 1 50 μg/ml and Glabridin 2.5 μM | 92.2 |
| 11 | AT-1 5 μM and Glabridin 2.5 μM | 95.2 |
| 12 | Extract* of Example 1 50 μg/ml and AT-1 5 μM and Glabridin 2.5 μM | 87.8 |

Note:

(i) The aqueous extract* was a co-extract of the following:

Plant 1: *Atractylodes macrocephala* - first active botanical ingredient was atractylenolide I, II and III (AT-1, AT-2, AT-3); and Plant 2: *Glycyrrhiza glabra* - second active botanical ingredient was licochalcone A and glabridin Plant 3: *Paeonia lactiflora* - third active ingredient was paeoniflorin Plant 4: *Poria cocos* - fourth active ingredient was pachymic acid.

(ii) #The lower the better

The data in Table 2 indicates that kojic acid is the most effective ingredient but it is the positive control. When the amount of the extract of Example 1 is increased from 50 to 300 μg/ml, there is a concomitant progressive reduction in melanin content. In fact, 300 pg/ml of the aqueous extract brings about more reduction in melanin content than kojic acid. However, this much amount of the extract would likely make the composition economically unviable and increase the likelihood of adverse/unwanted side effects.

The data pertaining to Reference numbers 7 to 11 indicates that the combinations of ingredients is not good enough because, in the case if combinations, the combined effect is an additive effect of the constituent ingredients.

However, the data pertaining to Refence number 12, which is in accordance with this invention, indicates that the combined effect is more than the expected or theoretical sum of the effect of 50 μg/ml of the extract* of Example 1, 5 μM of AT-1 and 2.5 μM Glabridin. Therefore, the combined effect is synergistic which indicates that the effect is an unexpected outcome.

The invention claimed is:

1. A composition comprising a plurality of active botanical ingredients, each predominantly associated with an in-use beneficial effect on an animate or inanimate substrate, where said composition comprises:

(i) a first aqueous extract of a material derived from a first plant, said first extract comprising a first amount of a first active botanical ingredient;

(ii) a second aqueous extract of a material derived from a second plant whose genus is not the same as the first plant, said second extract comprising a first amount of a second active botanical ingredient;

(iii) an additional amount of said first active botanical ingredient; and (iv) an additional amount of said second active botanical ingredient;

where each said additional amount is included by spiking said composition or the corresponding aqueous extract selectively with said first and said second active botanical ingredients, such that ratio of said first amount of said first active botanical ingredient to its corresponding additional amount and ratio of said first amount of said second active botanical ingredient to its corresponding additional amount in the composition is from 1:1 to 1:3000 parts by weight, wherein said composition is substantially free of non-aqueous extracts of any material derived from said first or said second plant, wherein said first plant is Atractylodes macrocephala and said first active botanical ingredient is atractylenolide I, II or Ill and further wherein said second plant is Glycyrrhiza uralensis, Glycyrrhiza inflata or Glycyrrhiza glabra and said second active botanical ingredient is licochalcone A or glabridin; and, wherein aqueous extract means that the extract is obtained only by using water as the solvent for extraction, wherein said composition further comprises another aqueous extract of a material derived from a third plant whose genus is not the same as the first or the second plant, where said third extract comprises a first amount of a third active botanical ingredient and an additional amount of said third active botanical ingredient included by spiking said composition or the corresponding aqueous extract selectively with said third active botanical ingredient, such that ratio of said first amount of said third active botanical ingredient to its corresponding additional amount in said composition is from 1:1 to 1:3000 parts by weight, wherein said composition is substantially free of non-aqueous extract of any material derived from said third plant wherein said third plant is Paeonia lactiflora and said third active botanical ingredient is paeoniflorin, further wherein said composition further comprises another aqueous extract of a material derived from a fourth plant whose genus is not the same as the first, second or third plant, where said fourth extract comprises a first amount of a fourth active botanical ingredient and an additional amount of said fourth active botanical ingredient included by spiking said composition or the corresponding aqueous extract selectively with said fourth active botanical ingredient, such that ratio of said first amount of said fourth active botanical ingredient to its corresponding additional amount in said composition is from 1:1 to 1:3000 parts by weight, wherein said composition is substantially free of non-aqueous extract of any material derived from said fourth plant wherein said fourth plant is Poria cocos and the fourth active botanical ingredient is pachymic acid.

2. A composition comprising a plurality of active botanical ingredients, each predominantly associated with an in-use beneficial effect on an animate or inanimate substrate, where said composition comprises:

(i) an aqueous co-extract of a material derived from a first plant and a material derived from a second plant whose genus is not the same as the first plant, said aqueous extract comprising a first amount of a first active botanical ingredient originating from said first plant and a second active botanical ingredient originating from said second plant;

(ii) an additional amount of said first active botanical ingredient; and, (iii) an additional amount of said second active botanical ingredient;

where each said additional spiked amount is included by spiking said composition or the aqueous co-extract selectively with said first and said second active botanical ingredients, such that ratio of said first amount of said first active botanical ingredient to its corresponding additional amount in the composition and ratio of said first amount of said second active botanical ingredient to its corresponding additional amount in the composition is from 1:1 to 1:3000 parts by weight, wherein said composition is substantially free of non-aqueous extracts of any material derived from said first or said second plant, wherein said first plant is Atractylodes macrocephala and said first active botanical ingredient is atractylenolide I, II or Ill and further wherein said second plant is Glycyrrhiza uralensis, Glycyrrhiza inflata or Glycyrrhiza glabra and said second active botanical ingredient is licochalcone A or glabridin, and, wherein aqueous extract means that the extract is obtained only by using water as the solvent for extraction, wherein said composition further comprises another aqueous extract of a material derived from a third plant whose genus is not the same as the first or the second plant, where said third extract comprises a first amount of a third active botanical ingredient and an additional amount of said third active botanical ingredient included by spiking said composition or the corresponding aqueous extract selectively with said third active botanical ingredient, such that ratio of said first amount of said third active botanical ingredient to its corresponding additional amount in said composition is from 1:1 to 1:3000 parts by weight, wherein said composition is substantially free of non-aqueous extract of any material derived from said third plant wherein said third plant is Paeonia lactiflora and said third active botanical ingredient is paeoniflorin, further wherein said composition further comprises another aqueous extract of a material derived from a fourth plant whose genus is not the same as the first, second or third plant, where said fourth extract comprises a first amount of a fourth active botanical ingredient and an additional amount of said fourth active botanical ingredient included by spiking said composition or the corresponding aqueous extract selectively with said fourth active botanical ingredient, such that ratio of said first amount of said fourth active botanical ingredient to its corresponding additional amount in said composition is from 1:1 to 1:3000 parts by weight, wherein said composition is substantially free of non-aqueous extract of any material derived from said fourth plant wherein said fourth plant is Poria cocos and the fourth active botanical ingredient is pachymic acid.

3. The composition as claimed in claim 1, wherein said composition is a detergent composition, a fabric conditioner or a hard-surface cleaning composition and said in-use beneficial effect is on an inanimate substrate.

4. The composition as claimed in claim 1 wherein said composition is a cosmetic, a food product, a beverage, an ice-cream or a frozen desert and said in-use beneficial effect is on an animate substrate.

5. The composition as claimed in claim 3, wherein said composition is a cosmetic composition and said in-use beneficial effect is a cosmetic effect.

6. The composition as claimed in claim 1, wherein said ratio is from 1:1 to 1:2500 parts by weight.

7. The composition as claimed in claim 1, wherein said first amount of said first active botanical ingredient and said first amount of said second active botanical ingredient is 0.00001 wt % to 5 wt %.

8. A The composition as claimed in claim 1, wherein each said additional amount is 0.00001 wt % to 10 wt % by weight of said composition.

9. A method for lightening the skin comprising the step of applying the composition of claim 1 to the skin.

10. A method for reducing melanin content of skin comprising the step of applying the composition of claim 1 to the skin.

11. The composition as claimed in claim 1, wherein said composition further comprises 0.1 to 10% by weight of said composition of a skin lightening agent comprising niacin, niacinamide, picolinamide, isonicotinamide, 12-HAS, conjugated linoleic acid, kojic acid, arbutin, resorcinol or a mixture thereof.

12. The composition as claimed in claim 1, wherein said composition further comprises 0.1 to 10% by weight of said composition of one or more inorganic or organic UV sunscreen.

* * * * *